United States Patent [19]

Subbiah

[11] Patent Number: 4,861,594
[45] Date of Patent: Aug. 29, 1989

[54] GUARANA SEED EXTRACT AND METHOD OF PREPARATION

[75] Inventor: M. T. Ravi Subbiah, Cincinnati, Ohio

[73] Assignee: University of Cincinnati, Cincinnati, Ohio

[21] Appl. No.: 26,102

[22] Filed: Mar. 16, 1987

[51] Int. Cl.$^4$ .............................................. A61K 35/78
[52] U.S. Cl. ................................ 424/195.1; 514/822; 426/428
[58] Field of Search ...................... 424/195.1; 514/822; 426/428

[56] References Cited
PUBLICATIONS

Chem. Abst. 107:196581k, 1987.
Chem. Abst. 104:128329x, 1986.
Chem. Abst. 89:89063f, 1978.

Primary Examiner—John W. Rollins
Attorney, Agent, or Firm—Frost & Jacobs

[57] ABSTRACT

A method of preparing a composition capable of inhibiting platelet aggregation in mammalian blood induced by adenosine diphosphate or arachidonic acid, which comprises forming an aqueous extract of dried and powdered seeds of the plant *Paullinia cupana* (guarana), centrifuging the solution and filtering the supernatant. A fraction of this aqueous extract obtained by thin-layer chromatographic fractionation on silica gel plates, which is free of salicylic acid, xanthines and nicotinic acid, is capable of deaggregating platelet aggregations in mammalian blood induced by adenosine diphosphate or arachidonic acid as well as inhibiting platelet aggregation. This fraction is eluted with ethanol, and centrifuged to removed gel. The supernatant may be dried and reconstituted with distilled water.

6 Claims, 3 Drawing Sheets

GUARANA SEED EXTRACT AND METHOD OF PREPARATION

BACKGROUND OF THE INVENTION

This invention relates to the preparation by thin-layer chromatographic fractionation of an aqueous extract from seeds of the plant *Paullinia cupana* H.B.K. (guarana) which possesses biological activity, more particularly an ability to inhibit platelet aggregation in mammalian blood and to deaggregate platelet aggregates induced by adenosine diphosphate (ADP) and/or arachidonic acid. Formation of thromboxane $B_2$ is also inhibited by the extract of this invention, thus indicating utility in the treatment of thrombosis and other vascular disorders involving platelet aggregation.

Blood platelets are small cells present in large numbers in mammalian blood and are vital in arresting bleeding by aggregating to form a platelet plug. When bleeding does not occur, internal injury to a blood vessel wall may cause formation of a platelet plug which is called a thrombus. Thrombus formation bay block the flow of blood to an organ and cause infarction, a condition termed thrombosis. Thrombosis is considered to be a contributing cause to strokes, pulmonary embolisms, and myocardial infarctions. It is thus believed that ability to inhibit platelet aggregation and to deaggregate platelet aggregates would be of great benefit in reducing the adverse effects of thrombotic episodes.

The tropical plant guarana has been harvested in the Amazon basin for many years. Treatment of the seeds of this plant, and uses thereof in the form of syrups, extracts and distillates as flavoring agents and as a source of caffeine in the soft-drink industry are described by A. R. Henman in *Guarana (Paullinia Cupana Var. Sorbilis): Ecological And Social Perspectives On An Economic Plant Of The Central Amazon Basin,* Jour. of Ethnopharmacology 6 (1982) 311–338. It is stated therein that recently "... claims have been made for guarana's suitability as a tea and coffee substitute, particularly for those suffering from cardiovascular afflictions, and this could be related to the counterbalance given to the stimulant alkaloids in the drug by the saponins which are so well represented in the plant family which includes guarana (the Sapindaceae)."

F. Belliardo et al., in *HPLC Determination of Caffeine and Theophylline in Paullinia cupana Kunth (Guarana) and Cola spp.* Samples, Z. Lebens Unters Forsch (1985) 180:398–401 (Springer-Verlag), report quantitative estimations of caffeine and theophylline in guarana, commercial guarana and cola samples, by a reversed-phase, high-performance liquid-chromatographic method. Five different extraction procedures are disclosed, four of which involved, in general, suspending a sample in distilled water containing ammonia, hydrochloric acid, or ammonia plus chloroform; or in ethanol (70%), followed by boiling or heating under reflux, extraction with chloroform, drying the chloroform extracts over magnesium sulfate, evaporating to dryness in vacuo, dissolving the residue in a 1:1 methanol-water mixture acidified with hydrochloric acid, and diluting to volume. The fifth method, which gave the best recovery, comprised suspending a sample in distilled water (20 ml) containing 1 drop of concentrated HCl and 10 ml. of an aqueous solution of 8-chlorotheophylline (0.376 mg/ml) as an internal standard, heating under reflux for 15 minutes, cooling, centrifuging (4000 rpm for 10 minutes), separating the aqueous phase, washing the residue with aqueous acid solution, and diluting the combined aqueous solutions with $H_2O$ to a volume of 100 ml. Before HPLC analysis the solution was filtered. Analytical determination was done with a Perkin-Elmer Series 3B liquid chromatograph.

Synthetic compounds stated to be useful in inhibiting platelet aggregation and/or as cardiovascular agents for treatment of thrombotic conditions are disclosed in the following U.S. patents:

No. 4,593,029, issued June 3, 1986 to M C. Venuti et al, discloses $\omega$-(N-imidazolyl) alkyl ethers of unsubstituted or substituted 1,2,3,5-tetrahydroimidazo [2,1—b]] quinazolines.

No. 4,588,741, issued May 13, 1986 to M. Nakane, discloses thiabicycloheptane substituted amino prostaglandin analogs.

No. 4,581,369, issued Apr. 8, 1986, to Mr. Tsuruda et al, discloses imidazole derivatives, such as $\omega$-(2,4,6-trimethylphenyl)-3-(1 1-imidazolyl) benzenemethanol.

No. 4,575,512, issued Mar. 11, 1986 to S. E. Hall et al, discloses 7-oxabicycloheptane substituted oxa prostoglandin analogs.

No. 4,568,676, issued Feb. 4, 1986 to J. B. Smith discloses a method of inhibiting platelet aggregation by administering in combination a thromboxane systhetase inhibitor and an inhibitor of cyclic AMP phosphodiesterase, allegedly obtaining a synergistic effect.

No. 4,563,537, issued Jan. 7, 1986 to R. C. Larock, discloses thiophere-containing bicyclic prostaglandin endoperoxide analogs, synthesized by an addition reaction of a thienylpalladium to bicyclic alkenes.

Japanese patent application, public disclosure No. 227277/1984, published Dec. 20, 1984, discloses a method for producing a beverage containing guarana extract, wherein guarana seeds are placed in "potable alcohol" (presumably ethanol) for a number of days at room temperature, and the alcoholic extract is admixed with the main ingredients of the beverage, i.e. water and sweetening agents. The beverage may be carbonated, and contains about 1% alcohol.

Commonly used products for inhibiting blood platelet aggregation include aspirin, Dipyridamole, Anturan, and the like. However, many of the known products may exhibit other adverse physiological effects, and the antiaggregating action may be transient. Moreover, to the best of applicants' knowledge, there has been no suggestion in the prior art of an agent which has the ability to deaggregate platelet aggregates either in vitro or in vivo.

There is a definite need for a composition which can be produced simply and inexpensively and which can be administered orally or intravenously for deaggregation of platelet aggregates.

SUMMARY OF THE INVENTION

It is a principal object of the invention to provide a composition which produces no apparent undesirable side effects when administered in vivo, and which has the ability to deaggregate blood platelet aggregates, as well as to inhibit platelet aggregation.

The above and other objects of the invention are achieved, at least with respect to aggregations induced by ADP and/or arachidonic acid, by thin layer chromatographic fractionation of an aqueous extract of guarana seeds prepared in accordance with the present invention.

In accordance with the invention there is provided a method of preparing a composition capable of inhibiting platelet aggregation in mammalian blood and deaggregating platelet aggregations therein induced by at least one of adenosine diphosphate and arachidonic acid, comprising the steps of:

preparing an aqueous extract of dried and powdered seeds of the plant Paullinia cupana;

subjecting the aqueous extract to thin-layer chromatographic fractionation on 250 μm silica gel G plates to obtain a fraction from the first bank (origin) having an RF value of 0.03 to 0.1 as herein described;

dissolving said fraction in a solvent consisting essentially of chloroform and ethanol, whereby to free said fraction of salicylic acid, zanthines and nicotinic acid;

eluting the so dissolved fraction with ethanol; and centrifuging the eluate in order to remove gel.

The embodiment of the method described above may include the further steps of drying the supernatant from the final centrifuging step, and reconstituting the dried supernatant with distilled water in a quantity sufficient to provide an effective amount of the dried supernatant.

The initial or crude aqueous extract utilized in the embodiment of the method described above may be prepared by adding about 10 parts by weight of dried and powdered seeds of the plant Paullinia cupana to about 90 parts by weight distilled water either at room temperature or elevated temperature, centrifuging the resulting solution, and filtering the supernatant.

The invention further provides a composition capable of inhibiting platelet aggregation in mammalian blood and deaggregating platelet aggregations therein induced by at least one of adenosine diphosphate and arachidonic acid, comprising an effective amount of the centrifuged eluate having an RF of 0.03 to 0.1 prepared in accordance with the method described above, and a pharmaceutically acceptable carrier thereof.

The invention further provides a method of inhibiting platelet aggregation in mammalian blood and deaggregating platelet aggregations therein induced by at least one of adenosine diphosphate and arachidonic acid, which comprises administering to a mammalian host an effective amount of the centrifuged eluate having an RF value of 0.03 to 0.1 prepared in accordance with the method described above.

A method of inhibiting generation of thromboxane $B_2$ in platelets of mammalian blood from arachidonic acid comprises incubating platelets with arachidonic acid in vitro and analyzing the amount of thromboxane $B_2$ formed.

BRIEF DESCRIPTION OF THE DRAWINGS

Reference is made to the accompanying drawings wherein.

DETAILED DESCRIPTION OF THE INVENTION

Dried and powdered guarana seeds obtained from Drogasil S.A.-Laboratorio, Sao Paulo SP, Brazil were dissolved in distilled water in a 10% concentration by weight, at room temperature. After dissolution, which can be completed in about 30 minutes, the solution was centrifuged at 3000 rpm for 10 minutes, and the supernatant was filtered through common filter paper. This aqueous extract was used for assays in vitro and in vivo, and for chromatagraphic fractionation, as described hereinafter.

A portion of the aqueous extract was boiled for +minutes in order to determine the effect of boiling on the active ingredients in the extract.

Fractionated extracts were also prepared by subjecting an aqueous extract of dried and powdered guarana seeds (10% concentration by weight) to thin-layer chromatography on 250 μm silica gel G plates (from Analabs, North Haven, Conn.), and several fractions were separated and dissolved in a solvent consisting of chloroform and 96% ethanol in a 9:1 ratio, v/v. Such a system has been used in the prior art for separation of different methyl zanthines, as reported by K. Randerath, in "Thin Layer Chromatography", page 84 (1963) New York: Academic Press.

Prior to chromatographic separation, pure standards for caffeine, theophylline, theobromine and nicotinic acid (from Sigma Chemical Co., St. Louis, Mo.) were spotted along the side of the samples and were detected after spraying the chromatogram with a solution of 1.0 g iodine and 1.0 g potassium iodide in 100 ml ethanol, then with a solution of 25% hydrochloric acid and 96% ethanol in a 1:1 ratio, v/v. Different fractions were scraped and eluted with 96% ethanol. Each eluate was centrifuged at 3000 rpm in order to remove gel. Each supernatant was dried under nitrogen, and the dried residue was reconstituted with 750 μl of distilled water.

The concentrations of the 4 different fractions were: band 1, 26 mg/ml; band 2, 4.6 mg/ml; band 3, 9 mg/ml; and band 4, 2.3 mg/ml. These were tested for their effect on platelet aggregation, as described below.

Figure 1:
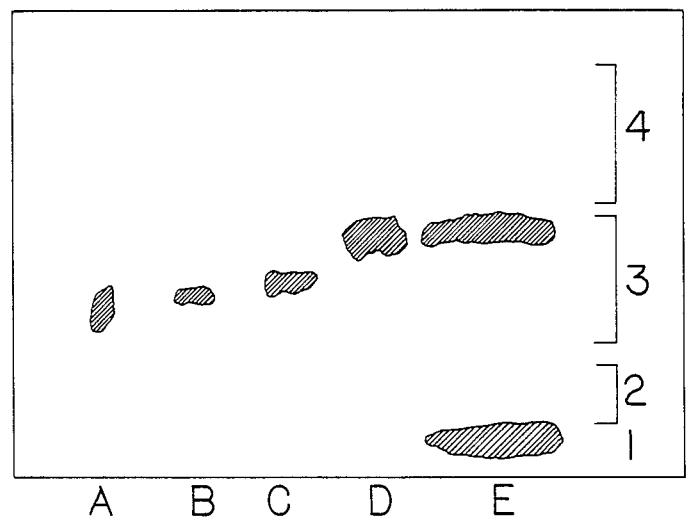
FIG. 1 is a thin-layer chromatogram of aqueous guarana extract.

The different fractions or bands are illustrated in FIG. 1 along with the above-mentioned pure standards for caffeine, theophylline, theobromine and nicotinic acid. These fractions can be identified or defined by their rate of migration, in relation to solvent front, during thin layer chromatography. This is the so-called RF value. Band or fraction 1 (having an RF value of 0.03-0.1) contained no salicylic acid, zanthines or nicotinic acid, as will be evident from FIG. 1. It occupied a relatively broad and well defined area. Fraction 3 (having an RF value of 0.22-0.57) was in the area corresponding to xanthines and nicotinic acid. As will be shown hereinafter, only fractions 1 and 3 exhibited inhibition of platelet aggregation, and fractions 2 and 4 are thus of no interest. The xanthines and nicotinic acid present in fraction 3 were partially responsible for the anti-aggregatory effect, and this fraction is thus not claimed herein. Fraction 1, on the other hand, exhibited a strong anti-aggregatory action and also promoted deaggregation, thus indicating the presence of other active agents, at present not identified, which migrated into the origin, i.e.. fraction 1.

Platelets from human volunteers and New Zealand rabbits (Harlan Animal Supplies, Indianapolis, Indiana) were used in the test described hereinafter. Human volunteers were instructed to abstain from any drugs for at least 7 days before the blood samples were taken. Blood was drawn from human volunteers by cubital venipuncture and from rabbits by cardiac puncture using ketamine/xylazine anesthesia. The blood samples were collected in 3.8% trisodium citrate (9:1, v/v).

Platelet-rich plasma was prepared by centrifuging the citrated blood for 15 minutes at 750 rpm. The remaining blood was centrifuged at 2500 rpm for 25 minutes in order to obtain platelet-poor plasma. Platelets were quantitated with an electronic counter (from Coulter Electronics, Inc., Hialeah, Fl.), and the platelet count was adjusted to 300,000 to 350,000/mm$^3$ with the platelet-poor plasma, and 0.45 ml of the adjusted plasma was used in each aggregation test.

Adenosine diphosphate (ADP) from Sigma Chemical Co., St. Louis, Mo., in a concentration of 0.1 mg/ml; arachidonic acid from NuCheck Preparations, Elysian, Minn. in a concentration of 1.0 mg/ml in 20 mM sodium carbonate; and collagen from Sigma Chemical Company in a concentration of 1.0 mg/ml were used as aggregatory agents. Blood samples were warmed to 37° C. with stirring for about 2 minutes prior to addition of 50 μl of aggregating agents. Guarana extract, or fractions thereof were added before the addition of ADP, arachidonic acid or collagen. The change in percentage light transmission was recorded with a dual aggregometer (from Chrono-Log Company, Havertown, Pennylvania) after the addition of aggregating agents.

In vitro studies were performed on both human and rabbit platelet rich plasma using crude aqueous guarana extract and fractions thereof. In addition, two different types of in vivo studies were done in rabbits. In the first study the effect of guarana on platelet aggregation was examined after intravenous injection, with 1.0 ml of aqueous extract being injected through a lateral ear vein and blood being collected before and 30 minutes after the injection. In the second study, 20 ml of guarana extract was injected through a nasogastric tube with blood being drawn before and 60 minutes after the injection. In both studies platelet aggregation was evaluated as described above.

Figure 2:
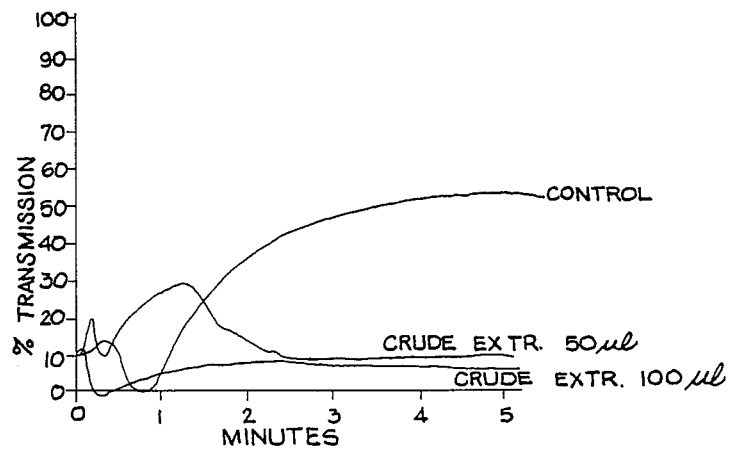
FIG. 2 is a graphic representation of the effect of aqueous guarana extract on human platelet aggregation induced by adenosine diphosphate in vitro.
Figure 3:
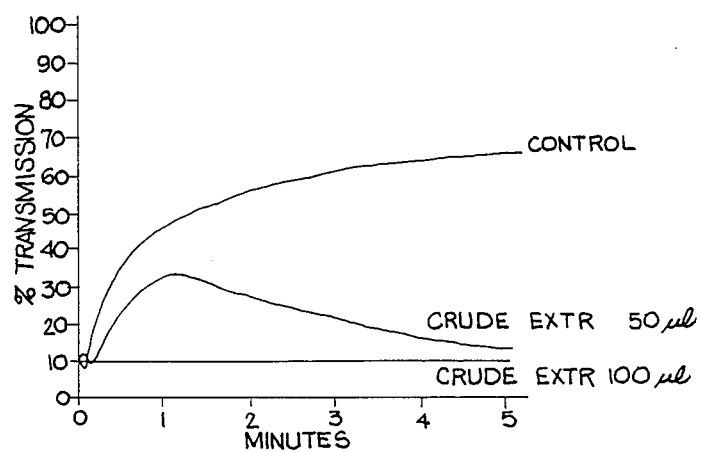
FIG. 3 is a graphic representation of the effect of aqueous guarana extract on human platelet aggregation induced by arachidonic acid in vitro.

FIGS. 2 and 3 show graphically the effect on human blood platelet aggregation in vitro of aqueous guarana extract prepared by suspending 10 parts by weight of dried and powdered seeds in 90 parts by weight distilled water, followed by centrifuging and filtration. FIG. 2 illustrates the effect on platelet aggregation induced by ADP while FIG. 3 illustrates the effect on platelet aggregation induced by arachidonic acid. In each figure a control is plotted along with the effect of an addition of 50 μl extract and 100 μl extract to each sample of 0.45 ml of plasma having a platelet count of 300,000–350,000/mm$^3$. It is evident in both FIGS. 2 and 3 that inhibition of aggregation was dose-related. With an addition of 50 μl extract, slight aggregation occurred for about 1 minute and decreased thereafter to a low level. On the other hand, with an addition of 100 μl extract there was virtually no aggregation from the outset of the test.

Although data are not shown, similar results were obtained with plasma of platelet-rich rabbit blood. Moreover, the samples of extract which ere boiled, as described previously, exhibited the same inhibiting effect.

Aggregation induced by addition of collagen was not inhibited by the guarana extract.

Table I summarizes in vivo tests in rabbits. In the case of intravenous injection of 1.0 ml of the aqueous extract of guarana a strong decrease in rabbit platelet aggregation induced either by ADP or by arachidonic acid was obtained. Table I also summarizes results from administration of the aqueous guarana extract to rabbits through a masogastric tube. A similar strong decrease in platelet aggregation was obtained.

The effect of various fractions of guarana extract prepared in accordance with the method of the invention is summarized in Table II. In these in vitro tests human blood platelets were used, and aggregation was induced both by ADP and arachidonic acid. It is evident from Table II that inhibition of platelet aggregation occurred with the aqueous extract of guarana seeds, fraction 1 (origin) and fraction 3, which is the area corresponding to xanthines and nicotinic acid, as will be apparent from FIG. 1. An addition of 0.05 ml of each fraction was made to each 0.45 ml sample of adjusted plasma.

Figure 4:
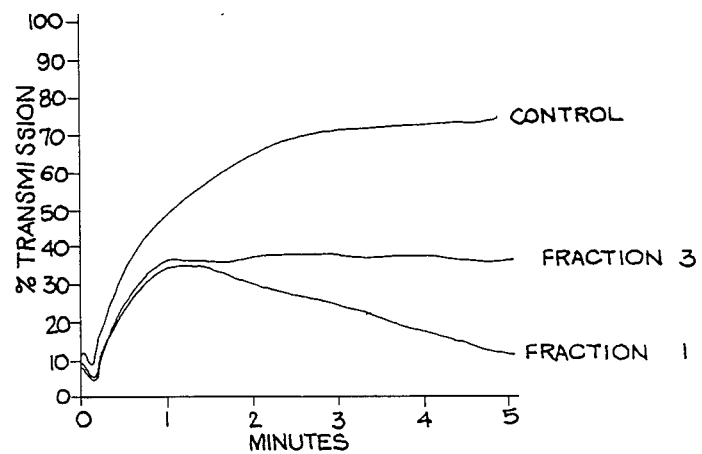
FIG. 4 is a graphic representation of the effect of two fractions of guarana extract on human platelet aggregation induced by adenosine diphosphate in vitro.

The test results in Table II were determined after 10 minutes incubation time. FIG. 4 is a plot of the same tests (using ADP only) for fractions 1 and 3 vs a control for a time period of 0 to 5 minutes. It is significant to note that the curves were different for fraction 1 (origin) and fraction 3. While fraction 3 (corresponding to xanthines and nicotinic acid) caused a decrease in platelet aggregation, fraction 1 (origin) also induced deaggregation of platelet aggregates.

Platelet thromboxane $B_2$ assays were conducted in accordance with the following procedures:

Platelet-rich plasma of rabbit blood was centrifuged at 1000 rpm for 20 minutes. Each resulting platelet pellet was washed twice in Tris-saline-glucose buffer (15 mmol Tris. HCl; 134 mmol NaCl; 5 mmol d-glucose) containing 1 mM EDTA pH 7.4, according to the method described by Skjaerlund et al, Biochemical Medicine 30, pages 357–362 (1983). After the second washing, the platelets were suspended in phosphate-buffered saline (137 mM NaCl; 2.7 mM KCl; 0.9 mM $CaCl_2$; 0.8 mM $MgCl_2.H_2O$; 6.5 mM $Na_2HPO_4.2H_2O$; 1.5 mM $KH_2PO_4$; 5.6 mM glucose; pH 7.4).

Prostaglandins generated by platelets were examined in accordance with the methods described by Gerrard et al, Journal Laboratory and Clinical Medicine 95, page 950–958 (1980) and WEY et al, Thrombosis and Haemostasis 48, pages 94–97 (1982), with some modifications. Aqueous extract of guarana and two fractions obtained by the preferred embodiment described above were added to 0.5 ml platelet suspension in 20 μl volume. After preincubation for 2 minutes at 37° C. in a shaking bath, 0.1 μCi of [$^{14}$C] arachidonic acid (obtained from New England Nuclear, Boston, Mass.; sp. act. 55.8 Ci/mol) was added in a 100 μl volume of 10 mmol $Na_2CO_3$. After 10 minutes incubation in a shaking bath at 37° C. the reaction was stopped by adding 0.5 ml 2M citric acid and 10 ml chloroform:methanol (2.:1 v/v). The lower organic layer was collected after the addition of 1.0 ml 0.9% NaCl. The extract was evaporated to a small volume under nitrogen followed by the addition of authentic standards for $PGF_{2\alpha}$, $PGE_2$ and $TxB_2$ as carriers. The various prostaglandins were separated by thin layer chromatography (250 μm silica gel G plates) using a solvent system of diethylether:methanol:acetic acid (135:5:3 v/v/v). Prior to separation pure standards for $PGF_{2\alpha}$, $PGE_2$ and $TxB_1$ were spotted along the side of the samples to permit visualization following a brief exposure to 2', 7'-dichlorofluorescein (0.1% in ethanol) spray. The areas corresponding to prostaglandins were scraped into vials, 10 ml of Aquasol-2 (from New England Nuclear) were added, and the areas were quantitated by liquid scintillation counter (Packard Tri Carb Counter) with automatic external standard for quench correction. The remaining areas of the gel were also scraped and counted in order to determine a percentage of recovery, which was in all cases greater than 75%. Results were expressed as dpm of incorporation/$2 \times 10^5$ platelets.

Table III summarizes the effect of guarana extract and fractions 1 (origin) and 3 on prostaglandin synthesis from [$^{14}$C] arachidonic acid. The main product recovered from the arachidonic acid metabolism was thromboxane $B_2$. The aqueous guarana extract as well as the two fractions reported in Table III promoted a decrease in thromboxane $B_2$ generation. A decrease in $PGF_{2\alpha}$ and $PGE_2$ generation was also obtained, although the changes were not significant.

Analysis for the presence of salicylates in all the above samples was negative, indicating the absence of salicylates in the guarana extract and fractions thereof. The test method was that disclosed by P. Trinder in *Biochemical Journal* 57, pages 301–303 (1954).

The reported values were analyzed using Student's test for unpaired means with the aid of a calculator program developed by Hewlett Packard. P-values equal to or less than 0.05 were considered as statistically significant.

The above results show that the effective agents in guarana extract and fractions 1 and 3 thereof are water-soluble, heat-resistant, and appear to be different from salicylatels. In the case of fraction 1, the effective agents further appear to be different from xanthines and nicotinic acid.

TABLE II

Human platelets - response to ADP and Arachidonic Acid
Effect of different fractions of guarana extract
(Mean of 2 tests)

| | % Transmission Change | |
|---|---|---|
| Fraction | ADP | Arachidonic Acid |
| None (control) | 65 | 68 |
| Crude guarana extract | 35 | 32 |
| Fraction 1 (RF 0.03–0.1) | 30 | 37 |
| Fraction 2 | 60 | 62 |
| Fraction 3 (RF 0.22–0.57) | 32 | 36 |
| Fraction 4 | 58 | 66 |

Fractions obtained by thin-layer chromatography (FIG. 1)

TABLE III

Rabbit platelets - conversion of [$^{14}$C] archidonic acid to prostaglandins
Effect of guarana extract and Fractions 1 and 3
(Mean values with their standard errors)

| | | Thromboxane $B_2$ | | Prostaglandin $F_2$ | | Prostaglandin $E_2$ | |
|---|---|---|---|---|---|---|---|
| Fraction | (n) | Mean | SEM | Mean | SEM | Mean | SEM |
| None (control) | 4 | 11,639 | 611 | 3,362 | 838 | 3,248 | 798 |
| Whol guar. extr. | 4 | 9,166* | 647 | 1,748 | 38 | 2,229 | 556 |
| Fraction 1 (RF 0.03–0.1) | 4 | 8,232** | 743 | 1,573 | 51 | 1,689 | 33 |
| Fraction 3 (RF 0.22–0.57) | 5 | 5,858** | 873 | 1,205* | 24 | 2,308 | 238 |

*$P < 0.05$
**$P < 0.02$
Fractions were obtained by thin-layer chromatography (FIG. 1).
Conversion in dpm/$2 \times 10^5$ platelets.

I claim:

1. A method of preparing a composition capable of inhibiting platelet aggregation in mammalian blood and deaggregating platelet aggregations therein induced by at least one of adenosine diphosphate and arachidonic acid, comprising the steps of:
preparing an aqueous extract of dried and powdered seeds of the plant Paullinia cupana by adding about 10 parts by weight of said seeds to about 90 parts by weight distilled water at room temperature for a time sufficient to complete dissolution, centrifuging and filtering the solution;
subjecting said aqueous extract to thin-layer chromatographic fractionation on 250 μm silica gel G plates to obtain a fraction from the first bank (origin) having an RF value of 0.03 to 0.1 as defined herein;
separating and dissolving said fraction obtained from the first band (origin) of said chromatographic fractionation in a solvent consisting essentially of chloroform and 96% ethanol in a 9:1 ratio, v/v.

TABLE I

Rabbit platelets - response to ADP and arachidonic acid
Effect of IV injection and oral ingestion of aqueous guarana extract
(Mean values with their standard errors)

| | | Transmission Charge | | | | | | |
|---|---|---|---|---|---|---|---|---|
| | | IV Injection | | | | Ingestion | | |
| | | Before | | After | | Before | | After | |
| Aggregation Agent | (n) | Mean | SEM | Mean | SEM | Mean | SEM | Mean | SEM |
| ADP | 3 | 36.67 | 0.88 | 11.00* | 2.86 | 39.67 | 0.33 | 18.50* | 6.06 |
| arachidonic acid | 3 | 48.33 | 1.20 | 0.10** | 0.06 | 47.67 | 0.88 | 2.50** | 1.44 |

*$P < 0.02$
**$P < 0.01$
Blood was collected before and 30 minutes after IV injection of 1.0 ml of guarana extract.
Blood was collected before and 6 minutes after 20.0 ml ingestion of quarana extract through a nasogastric tube.

whereby to free said fraction of salicylic acid, xanthines and nicotinic acid;
eluting said fraction with 96% ethanol; and
centrifuging the eluate at 3000 rpm in order to remove gel.

2. The method of claim 1, including the steps of drying the supernatant from said centrifuging, and reconstituting said dried supernatant with distilled water in a quantity sufficient to provide an effective amount of said dried supernatant.

3. The method of claim 2, wherein said supernatant is dried under nitrogen.

4. A composition capable of inhibiting platelet aggregation in mammalian blood and deaggregating platelet aggregations therein induced by at least one of adenosine diphosphate and arachidonic acid, comprising an effective amount of a centrifuged eluate having an RF value of 0.03 to 0.1 prepared in accordance with the method of claim 1, and a pharmaceutically acceptable carrier thereof.

5. A method of inhibiting platelet aggregation in mammalian blood and deaggregating platelet aggregations therein induced by at least one of adenosine diphosphate and arachidonic acid, which comprises administering to a mammalian host an effective amount of a centrifuged eluate having an RF value of 0.03 to 0.1 prepared in accordance with the method of claim 1.

6. A method of inhibiting generation of thromboxane $B_2$ in platelets of mammalian blood from arachidonic acid, which comprises incubating said platelets in vitro with an effective amount of a centrifuge eluate having an RF value of 0.03 to 0.1 prepared in accordance with the method of claim 1, in the presence of arachidonic acid.

* * * * *